(12) United States Patent
Valencia et al.

(10) Patent No.: US 10,953,397 B2
(45) Date of Patent: Mar. 23, 2021

(54) DIAGNOSTIC CHIP

(71) Applicant: HEWLETT-PACKARD DEVELOPMENT COMPANY, L.P., Houston, TX (US)

(72) Inventors: Melinda M. Valencia, San Diego, CA (US); Sirena Lu, Corvallis, OR (US); Chantelle Elizabeth Domingue, Corvallis, OR (US); Jeremy Sells, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 104 days.

(21) Appl. No.: 15/546,498

(22) PCT Filed: Jan. 30, 2015

(86) PCT No.: PCT/US2015/013731
§ 371 (c)(1),
(2) Date: Jul. 26, 2017

(87) PCT Pub. No.: WO2016/122577
PCT Pub. Date: Aug. 4, 2016

(65) Prior Publication Data
US 2018/0021776 A1 Jan. 25, 2018

(51) Int. Cl.
*G01N 27/02* (2006.01)
*B01L 3/00* (2006.01)
(Continued)

(52) U.S. Cl.
CPC ....... *B01L 3/502715* (2013.01); *B01L 3/5027* (2013.01); *G01N 33/48714* (2013.01);
(Continued)

(58) Field of Classification Search
None
See application file for complete search history.

(56) References Cited

U.S. PATENT DOCUMENTS

| 6,437,551 | B1 | 8/2002 | Krulevilch et al. |
| 7,619,739 | B1 * | 11/2009 | Sutherland ........... G01N 21/774 356/432 |

(Continued)

FOREIGN PATENT DOCUMENTS

| CN | 103403547 | 11/2013 |
| TW | 201120443 | 6/2011 |

(Continued)

OTHER PUBLICATIONS

Cheng; "Cell Detection and Counting Through Cell Lysate Impedance Spectroscopy in Microfluidic Devices"; May 11, 2007; www.rsc.org/loc—Lab on a Chip; pp. 746-755.

(Continued)

*Primary Examiner* — Paul S Hyun
(74) *Attorney, Agent, or Firm* — Fabian VanCott

(57) ABSTRACT

A system may comprise a voltage upconverter, a universal serial bus (USB) connector to receive an input voltage from a USB port on a computing device, and a microfluidic diagnostic chip communication link to electrically couple the voltage upconverter to a microfluidic diagnostic chip wherein the voltage upconverter is to convert the input voltage to be received by the USB connector to an output voltage sufficient to drive a pump on the microfluidic diagnostic chip. A diagnostic system may comprise a microfluidic diagnostic chip comprising a pump and a voltage upconverter to receive an input voltage from a universal serial bus (USB) port of a computing device and to convert the input voltage into an output voltage that powers activation of the pump.

17 Claims, 6 Drawing Sheets

(51) Int. Cl.
*G01N 33/487* (2006.01)
*H02M 3/155* (2006.01)

(52) U.S. Cl.
CPC ......... *H02M 3/155* (2013.01); *B01L 3/50273* (2013.01); *B01L 3/502753* (2013.01); *B01L 2200/0647* (2013.01); *B01L 2200/10* (2013.01); *B01L 2200/143* (2013.01); *B01L 2300/023* (2013.01); *B01L 2300/024* (2013.01); *B01L 2300/027* (2013.01); *B01L 2300/0663* (2013.01); *B01L 2300/088* (2013.01); *B01L 2400/046* (2013.01); *B01L 2400/0475* (2013.01)

(56) References Cited

U.S. PATENT DOCUMENTS

| 8,841,924 | B2 | 9/2014 | Reccius et al. | |
|---|---|---|---|---|
| 2004/0151962 | A1* | 8/2004 | Adams | H01M 8/04186 |
| | | | | 429/443 |
| 2005/0009101 | A1 | 1/2005 | Blackburn | |
| 2007/0024287 | A1 | 2/2007 | Graves et al. | |
| 2008/0022927 | A1 | 1/2008 | Zhang | |
| 2008/0105565 | A1* | 5/2008 | Davalos | B03C 5/005 |
| | | | | 205/775 |
| 2010/0075340 | A1 | 3/2010 | Javanmard | |
| 2010/0276017 | A1 | 11/2010 | Zhang et al. | |
| 2012/0088990 | A1* | 4/2012 | Bunge | A61B 5/14503 |
| | | | | 600/309 |
| 2012/0142032 | A1 | 6/2012 | Morgan et al. | |
| 2013/0288386 | A1 | 10/2013 | Fon et al. | |
| 2013/0295588 | A1 | 11/2013 | Watkins et al. | |
| 2014/0045701 | A1* | 2/2014 | Esfandyarpour | C12Q 1/6853 |
| | | | | 506/2 |
| 2014/0194313 | A1* | 7/2014 | Craighead | C12M 47/10 |
| | | | | 506/9 |
| 2015/0124012 | A1* | 5/2015 | Hays | B41J 2/07 |
| | | | | 347/9 |

FOREIGN PATENT DOCUMENTS

| TW | 201202704 | 1/2012 |
|---|---|---|
| TW | 201321745 | 6/2013 |
| WO | WO-2014160513 | 10/2014 |
| WO | WO-2014178827 | 11/2014 |

OTHER PUBLICATIONS

Gawad; "Micromachined Impedance Spectroscopy Flow Cytometer for Cell Analysis and Particle Sizing"; RSCPublishing; PubMed—NCBI; Aug, 13, 2001.

McGuinness; "Microfluidic Sensing Device"; Appln. No. PCT/US2014/0137848; Filed Jan. 30, 2014.

PCT International Search Report and Written Opinion; dated Oct. 21, 2015; PCT Application No. PCT/US2015/013731; Korean Intellectual Property Office; 15 pp.

* cited by examiner

US 10,953,397 B2

DIAGNOSTIC CHIP

BACKGROUND

Microfluidic devices comprise a number of microfluidic channels through which a fluid may be moved. In some examples, these devices implement pumps to drive the fluid through a channel or to eject the fluid out of an orifice.

BRIEF DESCRIPTION OF THE DRAWINGS

The accompanying drawings illustrate various examples of the principles described herein and are a part of the specification. The examples do not limit the scope of the claims.

Throughout the drawings, identical reference numbers designate similar, but not necessarily identical, elements.

DETAILED DESCRIPTION

Figure 1:
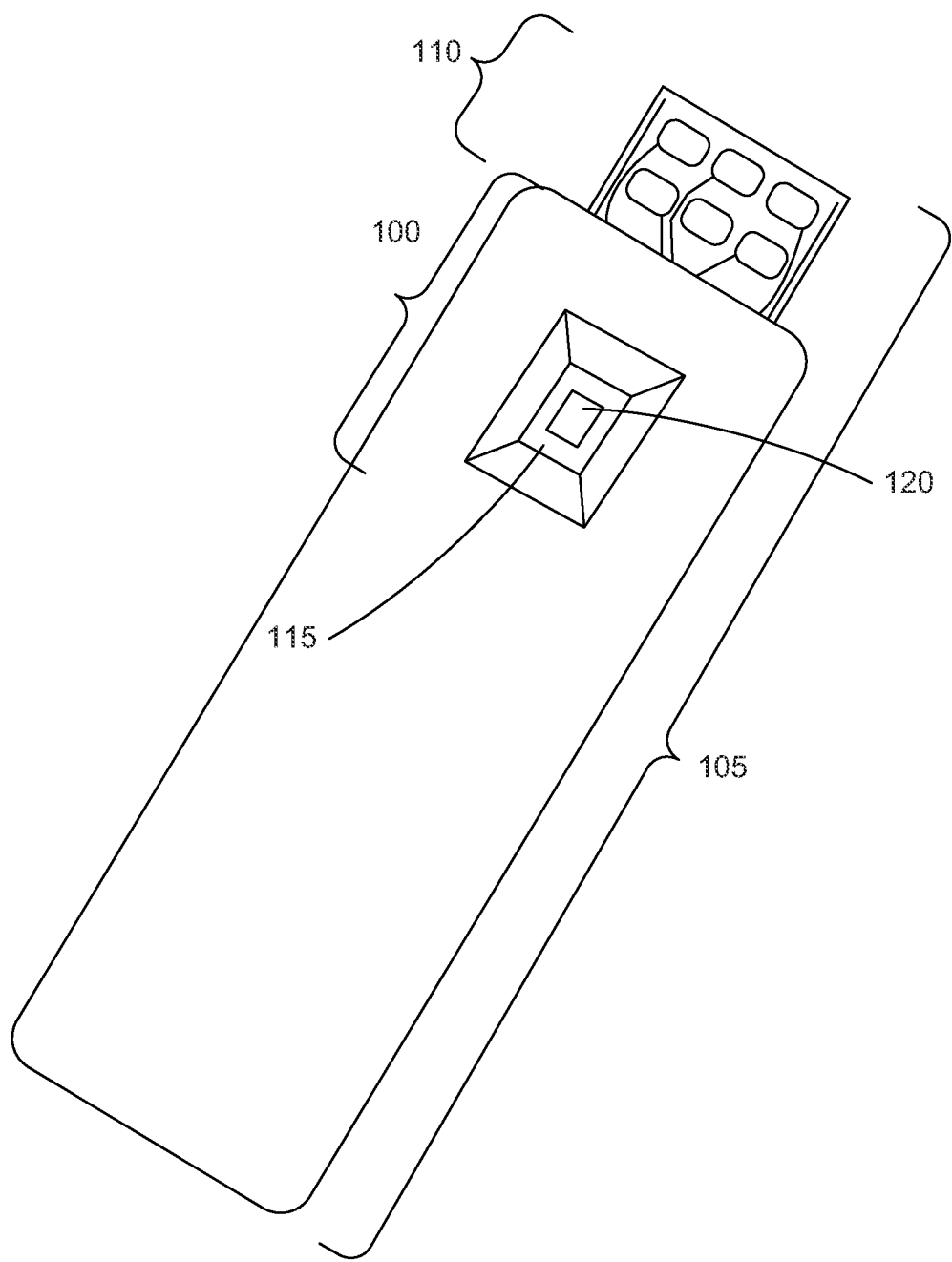
FIG. 1A is a diagram of a diagnostic system for powering a microfluidic diagnostic chip (MDC) according to one example of principles described herein.
FIG. 1B is a diagram of a diagnostic system for powering a microfluidic diagnostic chip (MDC) according to another example of the principles described herein.

As mentioned above, microfluidic devices such as a microfluidic diagnostic chip (MDC) may cause a fluid to be pumped through the microfluidic channels defined therein. Due to the high energy that is used to drive the pump, microfluidic devices implement power sources to drive the pumps. Often, the power sources may include utilizing a rechargeable or disposable battery pack or plugging the microfluidic device into an outlet to drive the pumps.

With advancing technology enabling electronic devices to be scaled to a smaller form factor, the demand for handheld portable devices is growing rapidly and moving away from electronic devices that are to be tethered to an outlet. As a result, a microfluidic device that includes an additional power source may be undesirable.

Examples described herein provide a system for powering a microfluidic diagnostic chip (MDC). The MDC may include a pump. The system may also include a voltage upconverter to receive electrical power from a universal serial bus (USB) port and convert the input voltage provided to an output voltage sufficient to drive the pump and sensor in the microfluidic diagnostic chip. Such a system may, for example, allow the voltage upconverter to drive the pump such that fluid is passed through microfluidic channels in the microfluidic diagnostic chip. As a result, a pump can pump the fluid and be portably driven by a voltage provided from the USB port. Further, this may, in some examples, eliminate the need for additional power sources providing sufficient power to drive the pump.

In the present specification and in the appended claims, the term "microfluidic device" or "microfluidic diagnostic chip (MDC)" is meant to be understood as a device that receives a fluid and causes the fluid to flow through, ejected out of, or circulated within a number of microfluidic channels defined therein. In one example, the microfluidic diagnostic chip may receive a fluid, e.g. a biologic fluid, including an analyte such as blood and flow that blood through microfluidic channels defined in the MDC. In one example, the microfluidic device is a printhead on a printer and may receive and eject an ink or fluid containing a biomarker out of a bore defined in microfluidic device. In yet another example, the MDC may be portable such that the MDC may easily be transported, by a user, to various locations. In still another example, the MDC may be powered using the voltage supplied by a USB port. In an additional example, the MDC may include a number of different microfluidic channel configurations for various applications involving pumping, ejection, and circulation of a fluid. In still an additional example, the MDC may include a warming mechanism to heat a fluid as well as nucleate the fluid to eject the fluid from the MDC.

In the present specification and in the appended claims, the term "voltage upconverter" means a mechanism to covert an input voltage received from a USB port to a higher output voltage to drive the microfluidic diagnostic chip (MDC). The voltage upconverter may include a number of circuit elements such as capacitors, resistors, inductors, diodes, and an integrated circuit (IC) such as a boost converter IC.

In the present specification and in the appended claims, the term "USB port" means a port that, with a cable or connector for communication between electronic devices, supplies electrical power to a microfluidic diagnostic device. In one example, the USM port implements a universal serial bus (USB) cable and connector as defined under the USB industry standard developed by Compaq, DEC, IBM, Intel, Microsoft, NEC, and Nortel. The USB port may connect a user device, such as a computer and a microfluidic diagnostic chip (MDC) to a voltage upconverter.

Further, as used in the present specification and in the appended claims, the term "a number of" or similar language is meant to be understood broadly as any positive number comprising 1 to infinity; zero not being a number, but the absence of a number.

In the following description, for purposes of explanation, numerous specific details are set forth in order to provide a thorough understanding of the present systems and methods. It will be apparent, however, to one skilled in the art that the present apparatus, systems, and methods may be practiced without these specific details. Reference in the specification to "an example" or similar language means that a particular feature, structure, or characteristic described in connection with that example is included as described, but may not be included in other examples.

Referring now to the figures, FIGS. 1A and 1B are diagrams of a diagnostic system for powering a microfluidic diagnostic chip (MDC) (108) according to two examples of principles described herein. As will be described below, the diagnostic system (100) comprises an MDC (108) with a pump (112) and a voltage upconverter (110) to receive electrical power from a USB connector and convert an input voltage provided by the USB connector to an output voltage sufficient to drive the pump in the MDC (112).

The MDC (108) may comprise a number of pumps that are supplied a voltage sufficient to drive the pumps and eject a fluid such as ink out of the device. Here, the voltage upconverter (100) described herein provides that voltage used to drive the pump similar to the voltage provided to the pumps in the MDC described herein. The voltage upconverter may receive a voltage from a USB connector, boost the voltage, and provide the boosted voltage to the MDC (108). In this example, a USB port (106) on a user device (102) is the source of the power supply provided to the USB connector (107) and relayed to the voltage upconverter (110) and is the sole source of power provided to the MDC through the voltage upconverter.

As illustrated, the diagnostic system (100) shown in FIGS. 1A and 1B includes a user device (102). The user device (102) may be a desktop computer, a laptop, a smartphone, a tablet, or other computing devices. Further, the user device (102) may be in communication with a voltage upconverter (110) via a USB port (106) on the user device (102) and a through USB connector (107) on the voltage upconverter (110). FIG. 1A shows the voltage upconverter (110) as a device separate from the user device (102) and MDC (108). FIG. 1B shows the voltage upconverter (110) as being part of the user device (102).

The voltage upconverter (110) may comprise an MDC communication link (114) to communicatively couple to an electrical connector (116) of the MDC (108). The user device (102) may send electrical signals, via the USB port (106), through the USB connector (107) and voltage upconverter (110), and to the electrical connector (116) associated with the MDC (108).

As will be described below, the electrical power from the USB port (106) is the sole electrical power provided to the voltage upconverter (110) and MDC (108). The USB port (106) may be a USB 1.x, a USB 2.0, or a USB 3.x standard. Additionally, the USB port (106) may use any type of connector interfaces to electrically couple the user device (102) to the voltage upconverter (110) including micro-B plug, UC-E6 plug, mini-B plug, standard-A receptacle, standard-A plug, standard-B plug, among others.

As illustrated, the diagnostic system (100) includes the MDC (108). The MDC (108) may be a device that analyzes and diagnoses a fluid including an analyte and provides feedback to, for example, the user device (102). The MDC (108) may be portable such that it can easily be transported, by a user, to various locations.

The MDC (108) includes a number of pumps (112). Depending on the type of MDC (108), the pumps (112) may be placed within a number of microfluidic channels defined in the MDC (108). In one example, each pump (112) may include a thin film resistor. The thin film resistor may be encapsulated with a passive film and a cavitation film. The resistor that forms the pump may be heated such that the fluid in the microfluidic channels are nucleated thereby creating a drive bubble. This drive bubble forms on the cavitation film of over the passive film and resistor. During operation of the pump, a voltage is applied to the resistor for a period of time. In one example, the period of time is 1-20 µs. The application of the voltage heats up the fluid rapidly to nucleate a drive bubble on the cavitation film. The drive bubble is thus created and collapses which constitutes the pumping mechanism by which the fluid is passed through the microfluidic channels. As will be described below, in some examples, each pump (112) may use 10 volts to drive the pump (112). Although, the present specification describes the pumps (112) as being driven using 10V, this is meant as an example and present specification contemplates the use of the voltage upconverter (110) to drive any type of pump (112). Consequently, any amount of voltage may be provided by the voltage upconverter (110).

The voltage upconverter (110) receives electrical power from the USB port (106) of the user device (102). The voltage upconverter (110) converts an input voltage provided from the USB port (106) and through the USB connector (107) to an output voltage sufficient to drive the pumps (112) in the MDC (108). Such a diagnostic system (100) allows the voltage upconverter (110) to drive the pumps (112) such that the fluid is passed through or ejected out of microfluidic channels in the MDC (108). As a result, the pumps (112) can pump the fluids and be portably driven by the USB port (106). In one example, the pumps (112) may be sequentially activated, one after another until the last is activated. In this example, pumping continues with firing a first pump (112) among the plurality of pumps (112) and continuing with the sequence of firing. The upconverting of the voltage eliminates the need for additional power sources implementing relatively higher voltages to drive the pumps (112). More information about the voltage upconverter (110) will be described below.

While this example has been described with reference to the voltage upconverter being either a separate standalone device (FIG. 1A) or located on the user device (102), the voltage upconverter may be located in any appropriate location according to the principles described herein. For example, the voltage upconverter may be located in the MDC (108), or any other external devices. Additionally, the voltage converter (110) of FIG. 1B does not show a USB connector (107) or MDC communication link (114) on the voltage upconverter (110). In this example, the voltage upconverter (110) may use a USB device (109) and a MDC communication link (114) present on the user device (102) in order to provide to the MDC (108) the voltage as described above.

Additionally, although the present specification describes providing a relatively high voltage to the MDC (108) in order to drive the pump (112) thereon, the voltage upconverter (110) along with the USB connector (107) may provide to the MDC (108) any number of varying voltages. In one example, a relatively higher voltage may be provided to the MDC (108) to drive the pump (112) while a relatively lower voltage may be provided to the MDC (108) to operate other devices associated with the MDC (108) such as sensors and other microfluidic analytical devices.

FIG. 2A is a block diagram of a voltage upconverter, according to one example of principles described herein. As described in connection with FIG. 1, the voltage upconverter (110) may include a USB connector (107) and a microfluidic chip (MDC) communication link (114). Any number of electrical components may be used to accomplish at least the functionality of receiving a voltage and boosting the voltage sufficiently to drive a number of pumps within a MDC (FIG. 1, 108). An example of such an arrangement of electrical components is shown in FIG. 2B.

FIG. 2B is a diagram of a voltage upconverter according to one example of principles described herein. As will be described below, a voltage upconverter may be a mechanism to covert an input voltage received from a USB port to a higher output voltage to drive a number of pumps of a MDC (FIG. 1, 108). The voltage upconverter may include a number of circuit elements such as capacitors, resistors, inductors, diodes, and an IC such as a boost converter.

As illustrated in FIG. 2B, the voltage upconverter (200) includes a boost converter IC (210). As will be described below a number of circuit elements such as capacitors, resistors, diodes, and inductors may be connected to various pins (214) of the boost converter IC (210). The pins (214) may be inputs or outputs. Further, the boost converter IC (210) may include a number of amplifiers such as an error amplifier and a current sensor. The boost converter IC (210) may further include a gate driver, a pulse width modulation (PWM) controller, a ramp generator, an oscillator, and a number of switches. More information about the boost converter IC (210) will be described in other parts of this specification.

As illustrated in FIG. 2B, the voltage upconverter (200) includes voltage input Vin (216). Vin (216) may connect the voltage upconverter (200) to the USB port (106) of the user device (102) shown in FIGS. 1A and 1B. Further, the USB device of FIGS. 1A and 1B may supply an input voltage of 5 volts, for example, to Vin (216). As will be described below, the 5 volts in this example may be sufficient to power the boost converter IC (210). Additionally, the 5 volts may be provided via the USB port (106). However, the present specification contemplates the use of other voltages provided by a USB port (106) and the 5 volts described herein is used as an example.

Further, Vin (216) may be connected to capacitors C1 (220-1) and C2 (220-2). Capacitors C1 (220-1) and C2 (220-2) may be used to reduce voltage ripples for Vin (216). As a result, capacitors C1 (220-1) and C2 (220-2) may aid Vin (216) to maintain a constant of 5 volts. In one example, capacitors C1 (220-1) and C2 (220-2) may each be 4.7 micro Farads (uF). Further, capacitors C1 (220-1) and C2 (220-2) may be tied to ground as illustrated.

As illustrated in FIG. 2B, the voltage upconverter (200) includes inductor L1 (222). L1 (222) determines how well the output voltage, Vout (218), holds its steady state. For purposes of driving the pump (FIGS. 1A and 1B) on the MDC (FIG. 1, 108) of FIG. 1, L1 (222) may be 12 micro henrys (uH). The input voltage may be applied across L1 (222). Further, L1 (222) stores the input voltage as energy as the inductor current ramps up.

Further, the voltage upconverter (200) includes diode D1 (226). When the inductor current rises to a threshold set by an error amplifier output, a power switch turns off in the boost converter IC (210) and D1 (226) is forward bias. This allows L1 (222) to transfer the stored energy to replenish capacitors C3 (220-3), C4 (220-4), and C5 (220-5). For purposes of driving the pump (FIGS. 1A and 1B) on the MDC (FIG. 1, 108) D1 (226) may be 40 volts.

The voltage upconverter (200) further includes a voltage divider (232). The voltage divider (232) may include two resistors such as R1 (224-1) and R2 (224-2). As illustrated, R1 (224-1) and R2 (224-2) are connected to the FB pin (214-3) of the boost converter IC (210). Further, R2 (224-2) is connected to ground as depicted. In one example, 10 volts is used to drive pumping on the pump (FIGS. 1A and 1B). The values for R1 (224-1) and R2 (224-2) determines a feedback voltage upon which the output voltage, Vout (218), is based on. Further, Vout (218) may be defined by equation 1:

$$Vout = Vfb(R1+R2)/R2 \qquad \text{equation (1)}$$

where Vfb (226) is the voltage applied to the FB pin (214-3) of the boost converter IC (210). Further, R1 may be resistor R1 (224-1) and R2 may be resistor R2 (224-2). As a result, R1 (224-1) is set to a resistance value of 10 kilo (K) ohms. R2 (224-2) is set to a resistance value of 1.4K ohms. As a result, Vout (218) is set to 10 volts. Although the present specification describes the output voltage (Vout) as being 10V, this output voltage (Vout) is merely meant as an example. Consequently, the present specification contemplates the use of any output voltage (Vout) sufficient to drive any number or types of devices located in the MDC (108) including the pumps (FIGS. 1A and 1B).

Further, Vout (218) is connected to other components of the MDC (FIGS. 1A and 1B, 108). As will be described in other parts of this specification, the output voltage of 10 volts for Vout (218) powers all components of the MDC of FIG. 1. For example, the output voltage drives a number of pumps (FIGS. 1A and 1B) within the MDC (FIGS. 1A and 1B, 108) to power the firing of the pumps (FIGS. 1A and 1B). Further, the output voltage may power components such as a logic board on the MDC (FIGS. 1A and 1B, 108), a timing circuit for timing the firing of the pumps (FIGS. 1A and 1B), other components, or combinations thereof.

As illustrated in FIG. 2B, the voltage upconverter (200) includes resistor R3 (224-3). R3 (224-3) may be connected to a voltage, V3 (228), and an EN pin (214-2) of the boost converter IC (210). The EN pin (214-2) may be an enable pin. When a voltage of the EN pin (214-2) falls below an enable threshold, as determined by R3 (224-3) and V3 (228), for more than 10 milliseconds, the boost converter IC (210) turns off. For purposes of driving the pumps (FIGS. 1A and 1B) on the MDC (FIGS. 1A and 1B, 108), R3 (224-3) may be 0 ohms. Further, V3 (228) may be 3 volts.

The voltage upconverter (200) further includes an RC circuit (230). The RC circuit (230) may include resistor R5 (224-5) and capacitors C6 (220-6) and C7 (220-7). Further, the RC circuit (230) may be connected to ground and a COMP pin (214-9) of the boost converter IC (210). The COMP pin (214-9) may be an output of an error amplifier of the boost converter IC (210). The RC circuit (230) may be connected to the COMP pin (214-9) to compensate a regulator of the boost converter IC (210). In one example, R5 (224-5) may be 4.42K ohms, C6 (220-6) may be 82 Pico Farads (pF), and C7 (220-7) may be 0.1 uF.

As illustrated in FIG. 2B, the voltage upconverter (200) includes capacitor C8 (220-8). C8 (220-8) may be tied to ground and a SS pin (214-8). The SS pin (214-8) may be an output of the boost converter IC (210). The SS pin (214-8) may be a soft start programing pin. Further, C8 (220-8) may be used to program soft start timing of the boost converter IC (210). In one example, increasing the soft start time reduces the overshoot during start up. Further, when the boost convert IC (210) is enabled, an internal bias current of 6 micro amps charges C8 (220-8) on the SS pin (214-8). The voltage at C8 (220-8) clamps the output of the error amplifier associated with the boost converter IC (210) that determines the duty cycle of PWM control of the boost converter IC (210). As a result, the input inrush current is eliminated. Once C8 (220-8) reaches 1.8 volts, the soft start cycle is completed and the soft start voltage no longer clamps the error amplifier's output. For a number of applications, a 47 nano Farad (nF) capacitor eliminates the output overshoot and reduces the peak inductor current. As a result, C8 (220-8) may be a 47 nF capacitor.

As illustrated in FIG. 2B, the voltage upconverter (200) includes resistor R4 (224-4). R4 (224-4) may be connected to ground and a FREQ pin (214-7) of the boost converter IC (210). The FREQ pin (214-7) may be an output switch frequency program pin. R4 (224-4) may be utilized to set a switch frequency. Increasing switching frequency reduces the value of external capacitors and inductors, but also reduces the power conversion efficiency. In one example, if R4 (224-4) is 80K ohms, the switch frequency may be set at 1200 kilohertz (kHz). If R4 (224-4) is 176K ohms, the switch frequency may be set at 600 kHz. For optimal performance R4 (224-4) may be 133K ohms. As a result, the switch frequency may be set around 800 kHz.

As illustrated, SW pins (214) of the boost converter IC (210) are connected to a switch side of L1 (222). Further, the SW pins (214) may be the switching node of the boost converter IC (210).

Further, a SYNC pin (214-4) of the boost converter IC (210) is connected to ground. The SYNC pin (214-4) may be a switch frequency synchronous pin. The SYNC pin (214-4) may use an external signal to set the boost converter IC's switch frequency. The switch frequency may be between 200 Hz and 2.2 megahertz (MHz). As illustrated, the SYNC pin (214-4) is connected to ground and is as short as possible to avoid noise coupling.

NC pin (214-10) of the boost converter IC (210) is a reverse pin. As illustrated NC pin (214-10) is connected to ground.

Further, the boost converter IC (210) includes a number of PGND pins (214-13 to 214-15). The PGND pins (214-13 to 214-15) are a power ground of the boost converter IC (210). Further, the PGND pins (214-13 to 214-15) may be connected to a source of a pulse width modulation (PWM) switch of the boost converter IC (210).

Further, the boost converter IC (210) includes an AGND pin (214-12). The AGND pin (214-12) may be a signal ground of the boost converter IC (210). As illustrated, the AGND pin (214-12) is connected to ground.

While this example has been described with reference to the voltage upconverter including a boost converter IC, the voltage upconverter may not include an IC. Rather, the voltage upconverter may include circuit elements that operate similarly to the boost converter IC, providing the circuit elements provide an output voltage sufficient to drive pumps (FIGS. 1A and 1B, 112) within a MDC (FIGS. 1A and 1B, 108).

Figure 3:
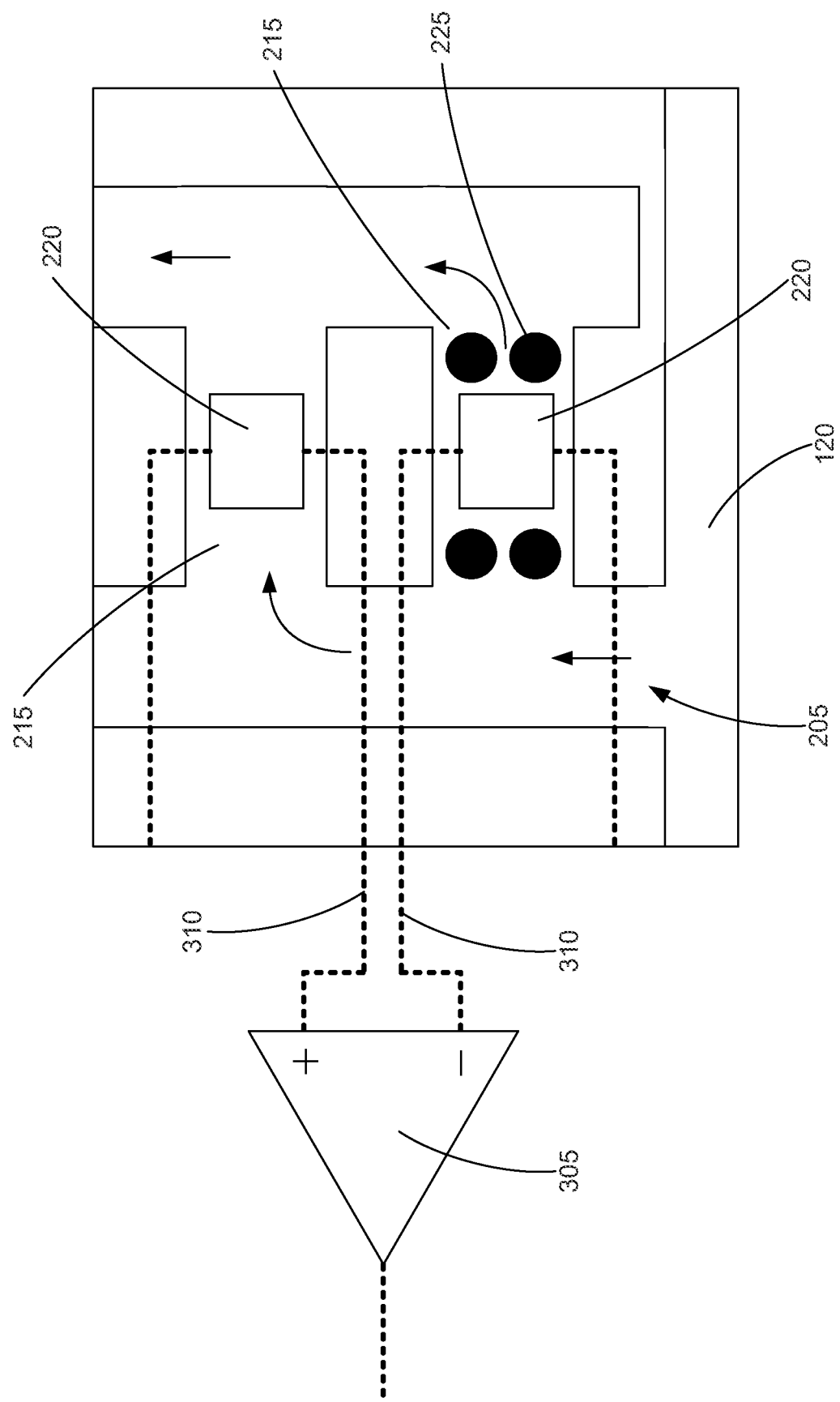
FIG. 3 is a diagram of a boost converter integrated circuit (IC) according to one example of principles described herein.

FIG. 3 is a diagram of a boost converter IC, according to one example of principles described herein. As mentioned above, a number of circuit elements such as capacitors, resistors, and inductors may be connected to various pins of the boost converter IC. The pins may be inputs or outputs.

As illustrated, a FB pin (314-3) and an EN pin (314-2) may be connected to inputs of an error amplifier (358). The error amplifier's output voltage fed back and compared to a stable reference voltage. Any difference between the two voltages generates a compensating error voltage. The EN pin (314-2) may provide the error amplifier (358) with a reference voltage of 1.229 volts. A feedback loop connected to the FB pin (314-3) regulates a reference voltage of the error amplifier (358). The output of the error amplifier (358) may be connected to a PWM controller (352) and a COMP pin (314-9). Further, when the inductor of FIG. 1 rises to a threshold set by the error amplifier's output, switch S1 (364) turns off. This forward biases the diode of FIG. 2B.

Further, the boost converter IC (300) may include a current sensor (360). The current sensor (360) may detect an electrical signal from the SW pin (314-5) and the PGND pin (314-13) and generate an output signal proportional to the detected electrical signal. As illustrated, resistor R1 (362) may bridge the inputs to the current sensor (360). Further, the output of the current sensor (360) may be connected to a ramp generator (354) and a PWM controller (352).

The boost converter IC (300) may further include gate driver (350). The gate driver (350) may be a power amplifier that receives a low-power input from a PWM controller (352) and produces a high-current. The high current may be used to drive S1 (364). As illustrated, S1 (364) is connected to SW pin (314-5), the gate driver (350), and R1 (362).

Further, the boost converter IC (300) may include a PWM controller (352). The PWM controller (352) may be used to control various electrical devices of the boost converter IC (300).

The boost converter IC (300) may further include a ramp generator (354). The ramp generator (354) may be connected to the output of the current sensor (360) and the PWM controller (352). The ramp generator (354) may be a function generator that increases its output voltage up to a specific value. Further, the ramp generator (354) may be connected to an oscillator (356).

The oscillator (356) may provide slope compensation. Slope compensation may be used to avoid sub-harmonic oscillation that is intrinsic to a current mode control at duty cycle higher than 50 percent. Further, if the inductor's value of FIG. 1 is less than 4.7 uH, the slope compensation may not be adequate. As illustrated, the oscillator (356) may be connected to a FREQ pin (314-7), a SYNC pin (314-4), and the PWM controller (352).

An example of the boost converter IC (300) will now be described. The PWM controller (352) turns on S1 (364) at the beginning of each switching cycle. The input voltage is applied across the inductor, L1 (222), of FIG. 2B and stores the energy as inductor current increases. During this portion of the switching cycle, the load current is provided by the output capacitor such as C3 (220-3), C4 (220-4), and C5 (220-5) of FIG. 2B. When the inductor current rises to the threshold set by the error amplifier's output, S1 (364) turns off and the diode, D1 (226), of FIG. 2B is forward biased. The inductor transfers stored energy to replenish the output capacitors and supply the load current. This operation repeats each every switching cycle. If S1 (364) is cycled fast, the inductor will not fully discharge. As a result, Vout of FIG. 2B will always see an output voltage greater than the input voltage Vin of FIG. 2B.

Figure 2:
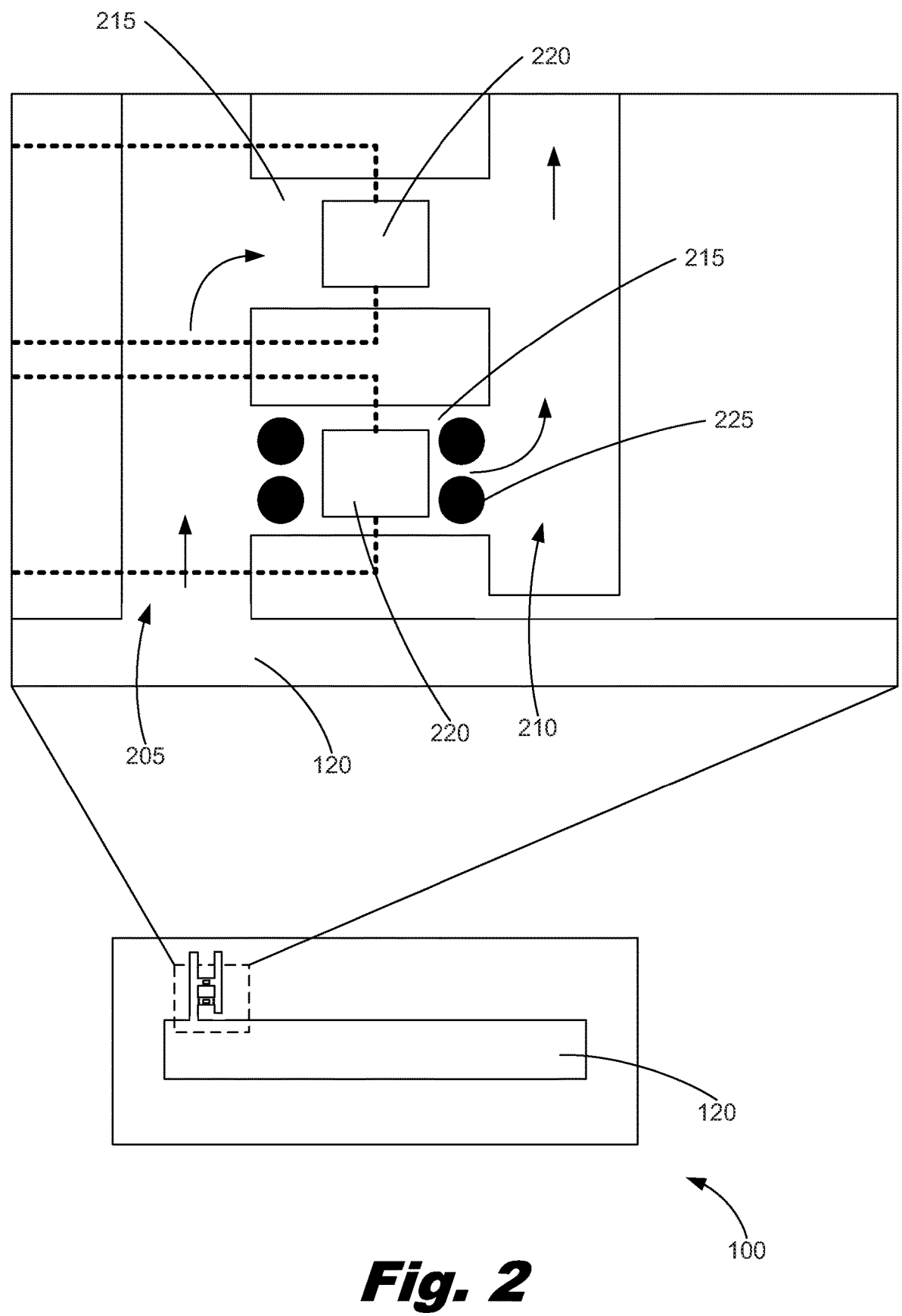
FIG. 2A is a block diagram of a voltage upconverter according to one example of principles described herein.
FIG. 2B is a diagram of a voltage upconverter according to one example of principles described herein.

Although FIGS. 2 and 3 show specific example diagrams of the voltage upconverter and boost converter integrated circuit (IC) respectively, the diagrams are merely examples and the present specification contemplates the use of any circuit that accomplishes the goals of the circuits described herein.

Figure 4A:
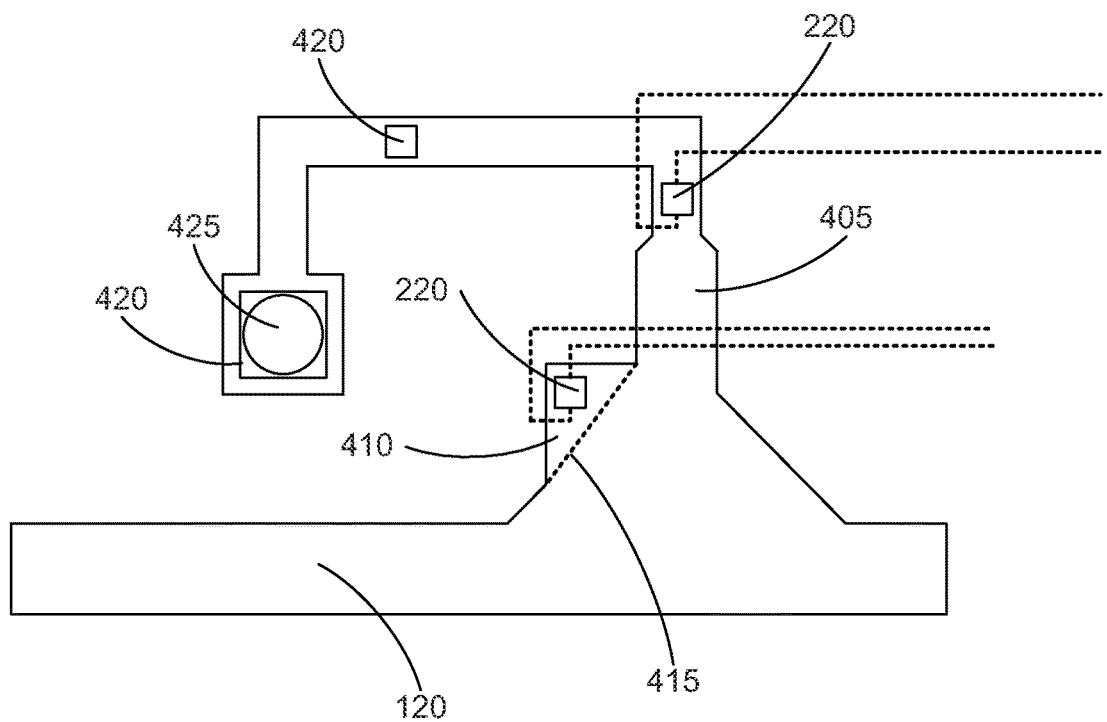
FIG. 4 is a flowchart a method for powering a microfluidic diagnostic chip according to one example of principles described herein.
Figure 4B:
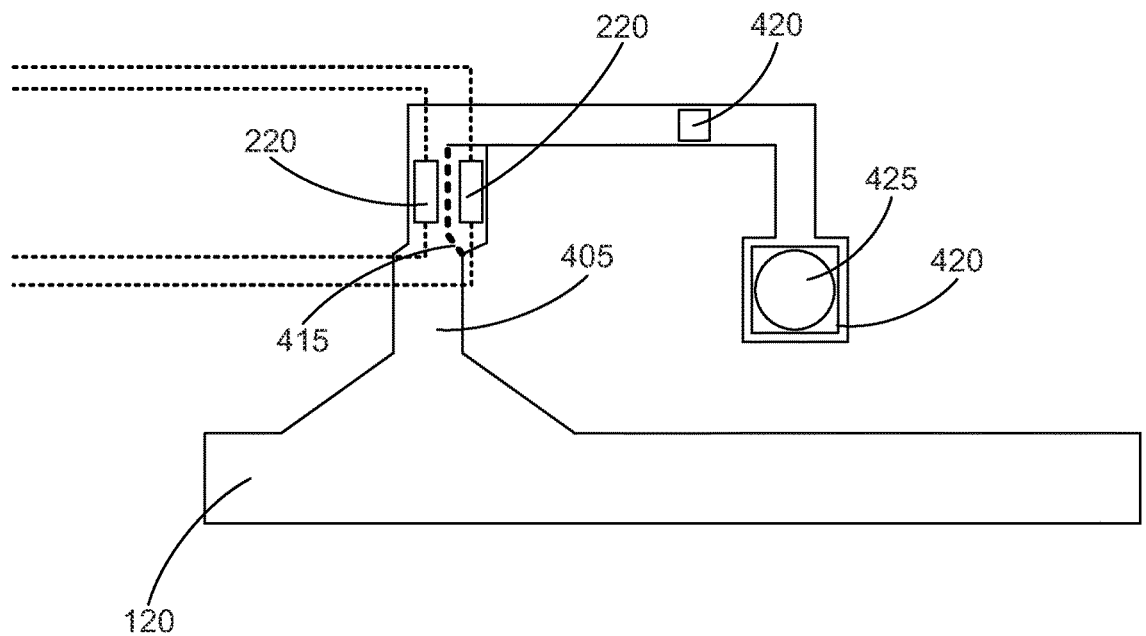

FIG. 4 is a flowchart showing a method for powering a microfluidic diagnostic chip according to one example of principles described herein. In one example, the method (400) may be executed by the system (100) of FIG. 1A or 1B. In this example, the method (400) includes receiving (401) electrical power from a USB port, converting (402) an input voltage of the electrical power to a relatively higher output voltage with a voltage upconverter, and activating (403) a pump (FIGS. 1A and 1B) on a MDC (FIGS. 1A and 1B, 108) using the output voltage.

As mentioned above, the method (400) includes receiving (401) electrical power from a USB port. The USB port may be a USB 1.x, a USB 2.0, or a USB 3.x standard. The maximum transfer rate of the USB 1.0 may be 1.5 megabits per second (Mbps) up to 12 Mbps.

A USB 2.0 may be backward compatible to a USB 1.x. Further, the maximum transfer rate of the USB 2.0 may be 480 Mbps. The charging power of the USB 2.0 may be 100 milliamps.

A USB 3.x may be backward compatible to a USB 1.x and a USB 2.0. Further, the maximum transfer rate of the USB 3.x may be 4.8 gigabits per second (Gbps). The USB 3.x may bi-directionally transfer data. The charging power of the USB 3.x may be 900 milliamps. As a result, the USB port may include various advantages and any specific USB port may be used to achieve certain qualities. However, USB port may supply the voltage upconverter with, for example, 5 volts as an input voltage. Further, the electrical power from the USB port may be the sole power provided to the MDC (FIGS. 1A and 1B, 108).

As mentioned above, the method (400) includes converting (402) an input voltage of the electrical power to a relatively higher output voltage with a voltage upconverter. As described above, the voltage upconverter converts the 5 volts supplied via the USB port as an input voltage and produces a relatively higher output voltage. As mentioned above, the relatively higher output voltage may be 10 volts. Further, the output voltage may be higher or lower than 10 volts depending on the electrical power sufficient to power the pumps (FIGS. 1A and 1B) of the MDC (FIGS. 1A and 1B, 108). For example, the output voltage may be 12 volts, 15 volts, 20 volts, 30 volts, or other output voltages.

As mentioned above, the method (400) includes activating (403) a pump (FIGS. 1A and 1B) on the MDC (FIGS. 1A and 1B, 108) using the output voltage. The MDC (FIGS. 1A and 1B, 108) includes a number of pumps (FIGS. 1A and 1B) used to pass a fluid through microfluidic channels defined in the MDC (FIGS. 1A and 1B, 108). To pump a fluid through the microfluidic channels in the MDC (FIGS. 1A and 1B, 108), the pumps (FIGS. 1A and 1B) receive an output voltage that may drive the activation of the pumps (FIGS. 1A and 1B). In some examples, an output voltage of 10 volts may be sufficient to drive the activation of the pumps (FIGS. 1A and 1B). As a result, the voltage upconverter may produce an output voltage of 10 volts.

Figure 5:
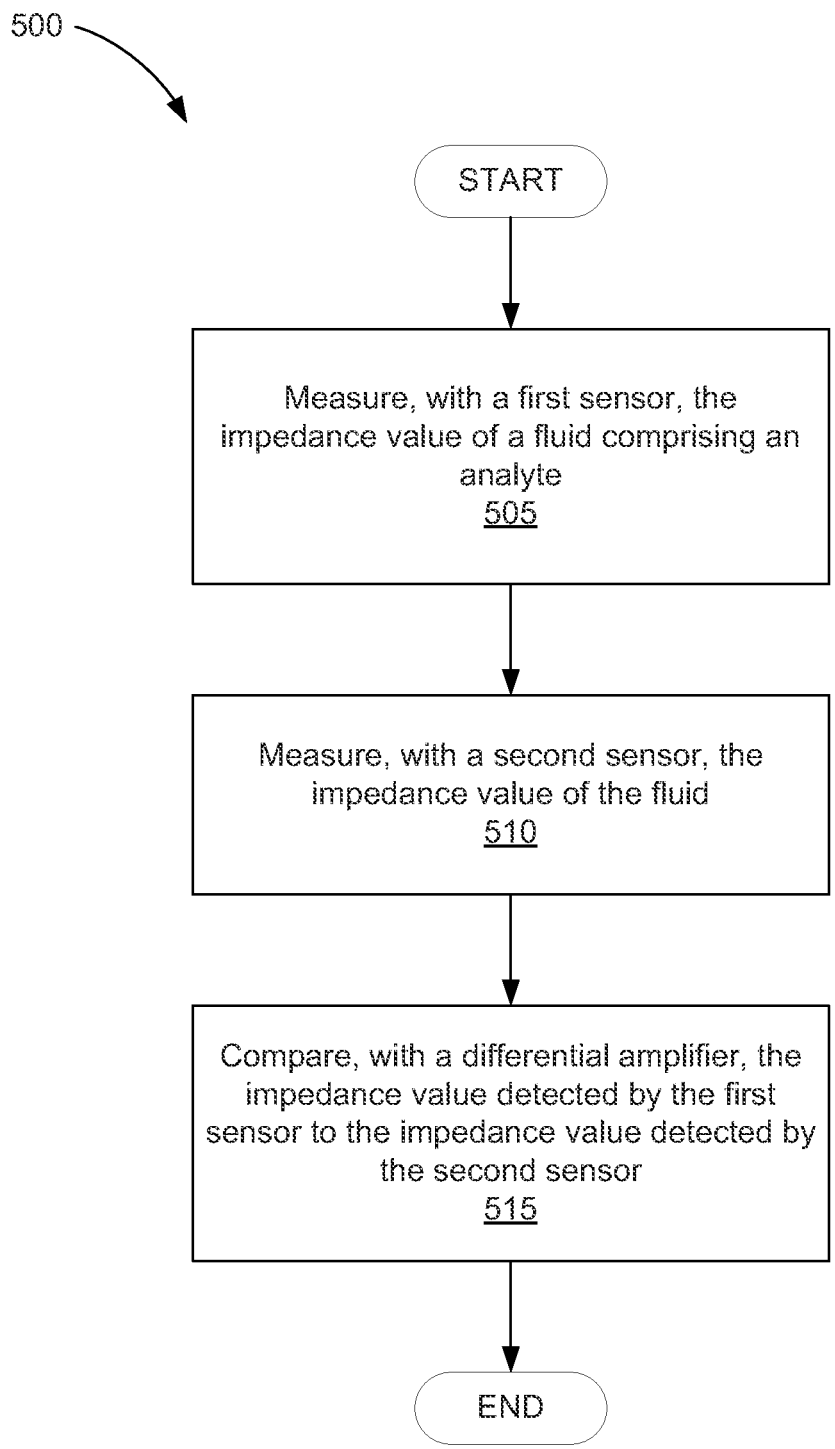
FIG. 5 is a flowchart of a method for powering a microfluidic diagnostic chip according to one example of principles described herein.
Figure 6:
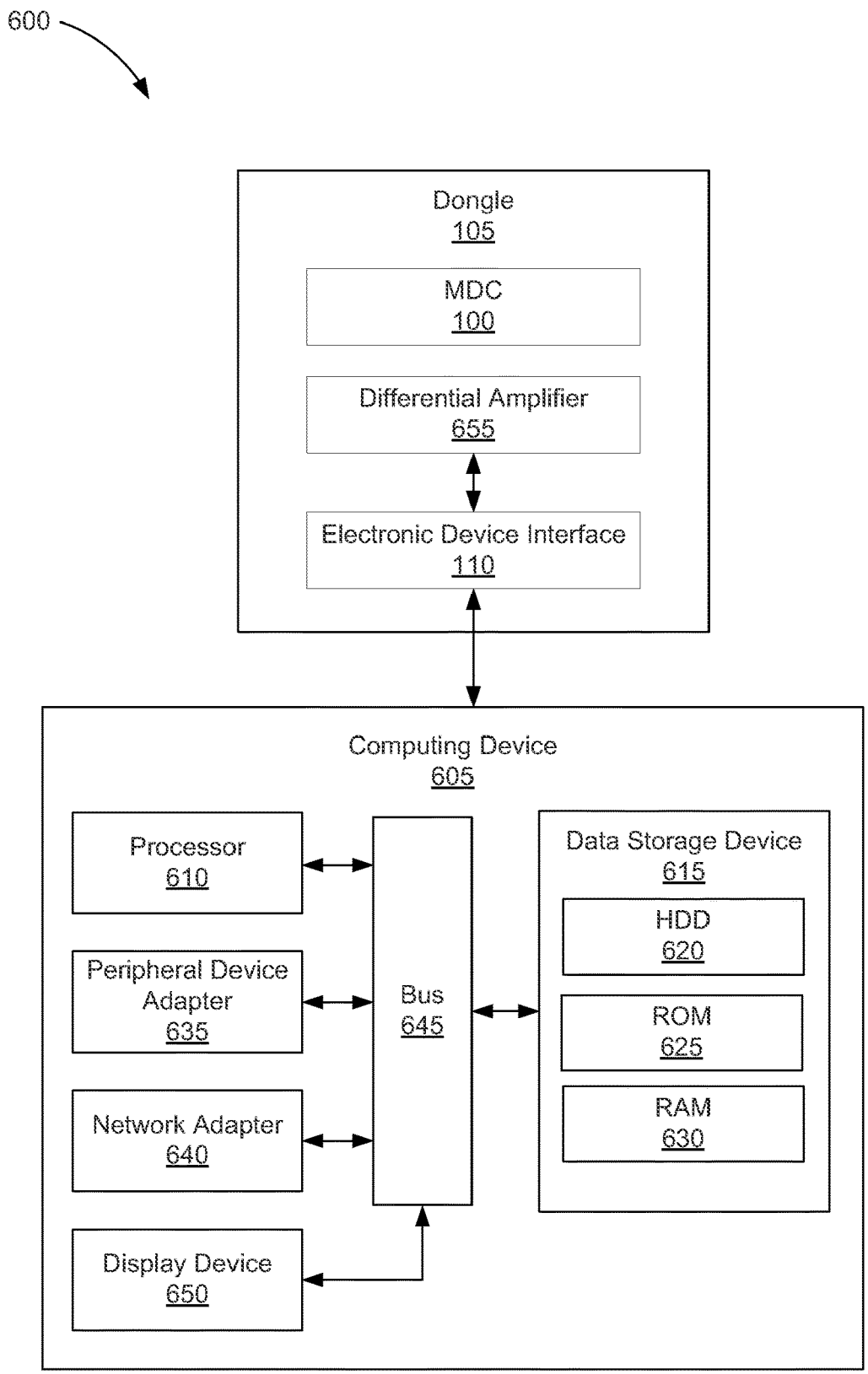

FIG. 5 is a flowchart of a method for powering a microfluidic diagnostic chip according to another example of principles described herein. In one example, the method (500) may be executed by the system (100) of FIG. 1A or 1B. In other examples, the method (500) may be executed by other systems such as system (200) of FIG. 2B. In this example, the method (500) includes receiving (501) electrical power from a USB port, converting (502) an input voltage of the electrical power to a relatively higher output voltage with a voltage upconverter, powering (503) with the output voltage a number of pumps (FIGS. 1A and 1B) within a MDC (FIGS. 1A and 1B, 108), and activating (504) the pumps (FIGS. 1A and 1B) on the MDC (FIGS. 1A and 1B, 108) using the output voltage.

As mentioned above, the method (500) includes powering (503) with the output voltage a number of pump (FIGS. 1A and 1B) within a MDC (FIGS. 1A and 1B, 108). As mentioned above, the output voltage of the voltage upconverter is connected to a number of pumps (FIGS. 1A and 1B) within the MDC (FIGS. 1A and 1B, 108). An output voltage of 10 volts may be sufficient to power the number of pumps (FIGS. 1A and 1B).

The preceding description has been presented to illustrate and describe examples of the principles described. This description is not intended to be exhaustive or to limit these principles to any precise form disclosed. Many modifications and variations are possible in light of the above teaching.

What is claimed is:

1. A microfluidic diagnostic chip, comprising:
    a number of input microfluidic channels;
    a number of output microfluidic channels;
    a number of interposing microfluidic channels, each fluidly coupled at one end to at least one input microfluidic channel and at a second end to at least one output microfluidic channel;
    first and second microfluidic sensors within the number of interposing microfluidic channels;
    a blocking device comprising a plurality of pillars to prevent particles of an analyte within the fluid from being sensed by the second microfluidic sensor, wherein the first microfluidic sensor measures an impedance of the fluid with particles and the second microfluidic sensor measures an impedance of the fluid without the particles;
    a bore; and
    a thermal resistor pump concentric to the bore to pump fluid through the bore, wherein the thermal resistor pump moves fluid across the first and second microfluidic sensors,
    wherein the microfluidic diagnostic chip is to compare output from the first microfluidic sensor sensing a fluid comprising an analyte to output from the second microfluidic sensor sensing the fluid lacking the analyte.

2. The microfluidic diagnostic chip of claim 1, further comprising a differential amp to receive signals from the first and second microfluidic sensors and compute a differential output.

3. The microfluidic diagnostic chip of claim 1, wherein the number of interposing microfluidic channels comprises a plurality of interposing microfluidic channels with the first and second microfluidic sensors each in a separate interposing microfluidic channel.

4. The microfluidic diagnostic chip of claim 3, further comprising a thin film resistor to pump the fluid through the input, output, and interposing microfluidic channels wherein the thin film resistor is encapsulated with a passive film and wherein the film resistor and passive film are encapsulated with a cavitation film.

5. The microfluidic diagnostic chip of claim 1, wherein the number of interposing microfluidic channels comprises a single interposing microfluidic channel with the first and second microfluidic sensors in the single interposing microfluidic channel.

6. The microfluidic diagnostic chip of claim 1, wherein the first and second microfluidic sensors measure impedance of the first fluid comprising the analyte and the second fluid without the analyte simultaneously.

7. The microfluidic diagnostic chip of claim 1, wherein the plurality of pillars of the blocking device traverse an interposing microfluidic channel.

8. The microfluidic diagnostic chip of claim 1, further comprising a slot to provide fluid to the number of input microfluidic channels.

9. The microfluidic diagnostic chip of claim 1, wherein the number of input channels is one channel, the number of output channels is one channel, and the number of interposing microfluidic channels is one channel.

10. The microfluidic diagnostic chip of claim 1, further comprising a pump to recirculate the fluid between the first microfluidic sensor and the second microfluidic sensor.

11. The microfluidic diagnostic chip of claim 1, wherein the first sensor and second sensor are in a single interposing microfluidic channel, the first sensor and second sensor are parallel to each other in the interposing microfluidic channel, the blocking device obstructs a portion of the interposing microfluidic channel.

12. A method of removing background noise from an impedance value of an analyte in a microfluidic diagnostic chip comprising a microfluidic channel, comprising:
    measuring, with a first sensor, an impedance value of a fluid comprising an analyte;
    passing the fluid through a blocking device on the microfluidic diagnostic chip, wherein the blocking device prevents passage of the analyte;

measuring, with a second sensor, an impedance value of the fluid without the analyte, wherein the first and second sensors are within the same microfluidic channel;

recirculating the analyte through the microfluidic channel; and comparing the impedance value detected by the first sensor to the impedance value detected by the second sensor.

13. The method of claim 12, wherein comparing the impedance value detected by the first sensor to the impedance value detected by the second sensor is performed with a differential amplifier.

14. A system, comprising:
a microfluidic chip comprising:
a first sensor;
a second sensor;
a number of particle blocking pillars around the second sensor to prevent particles from being sensed by the second sensor;
a bore in a microfluidic channel containing the first sensor;
a thermal resister pump around the bore to expel fluid through the bore; and
a differential amplifier communicatively coupled to or within the microfluidic chip;
wherein the first sensor is to measure an impedance value of the fluid comprising an analyte;
wherein the second sensor is to measure an impedance value of the fluid without the analyte; and
wherein the differential amplifier is to compare the impedance values received from the first and second sensors.

15. The system of claim 14, further comprising a second pump to recirculate the fluid between the first sensor and the second sensor.

16. The system of claim 14, wherein the second sensor is within a second microfluidic channel in the microfluidic chip, and wherein the first and second sensors are parallel relative to each other.

17. The system of claim 14, wherein the first sensor and second sensor are in a single interposing microfluidic channel and the first sensor and second sensor measure impedance simultaneously.

* * * * *